United States Patent [19]

Funderburg, Jr.

[11] Patent Number: 4,923,399
[45] Date of Patent: May 8, 1990

[54] DENTAL INSTRUMENT

[76] Inventor: Issac M. Funderburg, Jr., 1605 Fairy Dell, Lookout Mountain, Ga. 30750

[21] Appl. No.: 234,490

[22] Filed: Aug. 22, 1988

[51] Int. Cl.$^5$ .............................................. A61C 3/16
[52] U.S. Cl. ................................... 433/159; 433/153
[58] Field of Search ............... 433/159, 157, 156, 154, 433/153, 152

[56] References Cited

U.S. PATENT DOCUMENTS

| | | |
|---|---|---|
| 2,172,478 | 9/1939 | Machat . |
| 2,430,271 | 11/1947 | Brantley .............................. 433/159 |
| 2,848,812 | 8/1958 | Fuest ................................... 433/157 |
| 4,179,816 | 12/1979 | Anderson . |
| 4,197,647 | 4/1980 | Goldenthal . |
| 4,230,454 | 10/1980 | Lococo . |
| 4,474,500 | 10/1984 | Lynch . |

FOREIGN PATENT DOCUMENTS 8702573  5/1987  PCT Int'l Appl. .

Primary Examiner—Robert Peshock
Attorney, Agent, or Firm—Marshall, O'Toole, Gerstein, Murray & Bicknell

[57] ABSTRACT

The present invention provides a dental instrument for attachment to a tooth providing a stable support for the use of other dental instruments such as those used to remove crowns. The instrument comprises a pair of arms, pivotably joined, each arm having a handle portion and an adjustable instrument mounting handle portion and an adjustable instrument mounting head portion which includes opposable tooth gripping means and a tool suitable for providing a stable support for dental instruments. The invention also provides a method of removing dental prostheses such as crowns utilizing the dental instrument of the invention as a stable support for a dental instrument used to apply pressure to the margin between the tooth and crown.

8 Claims, 2 Drawing Sheets

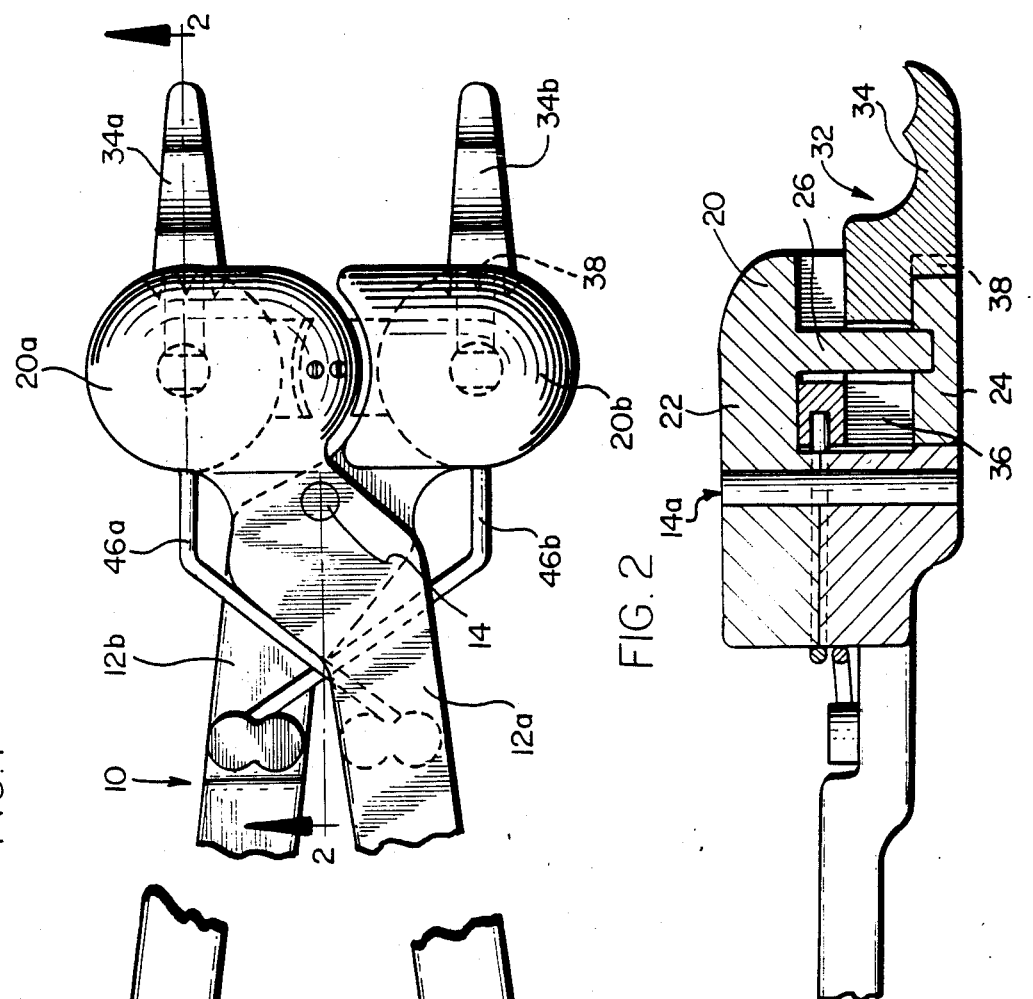
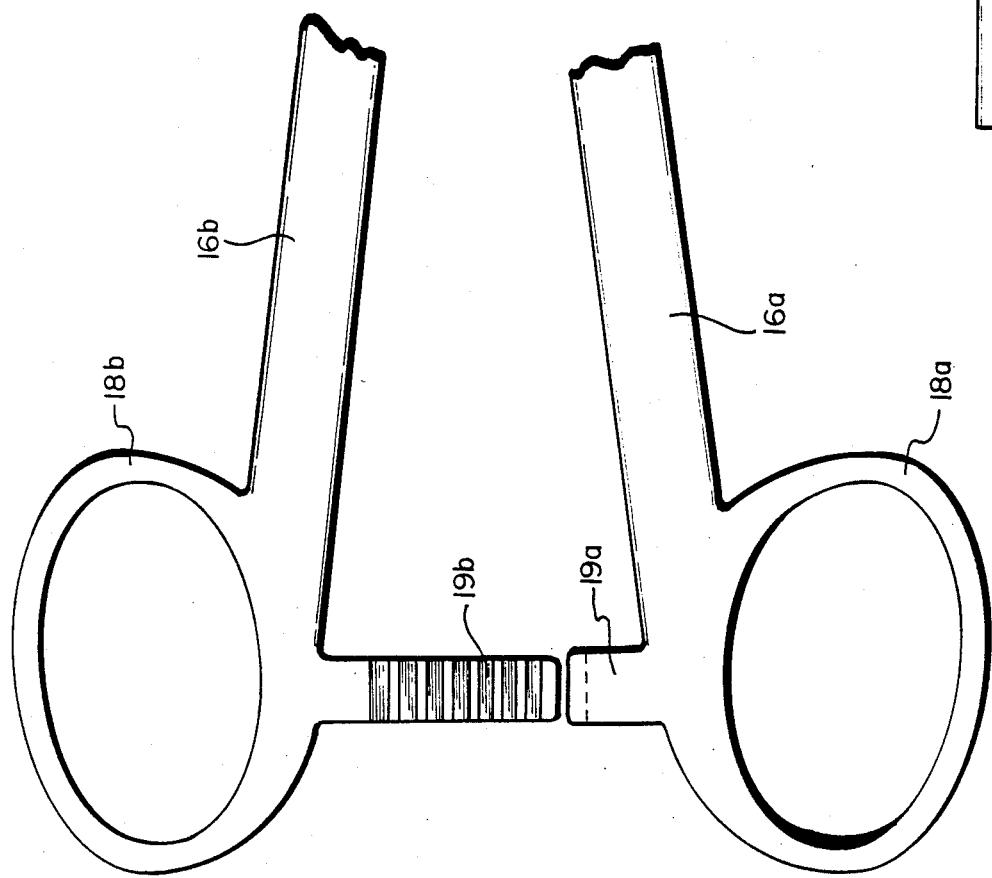

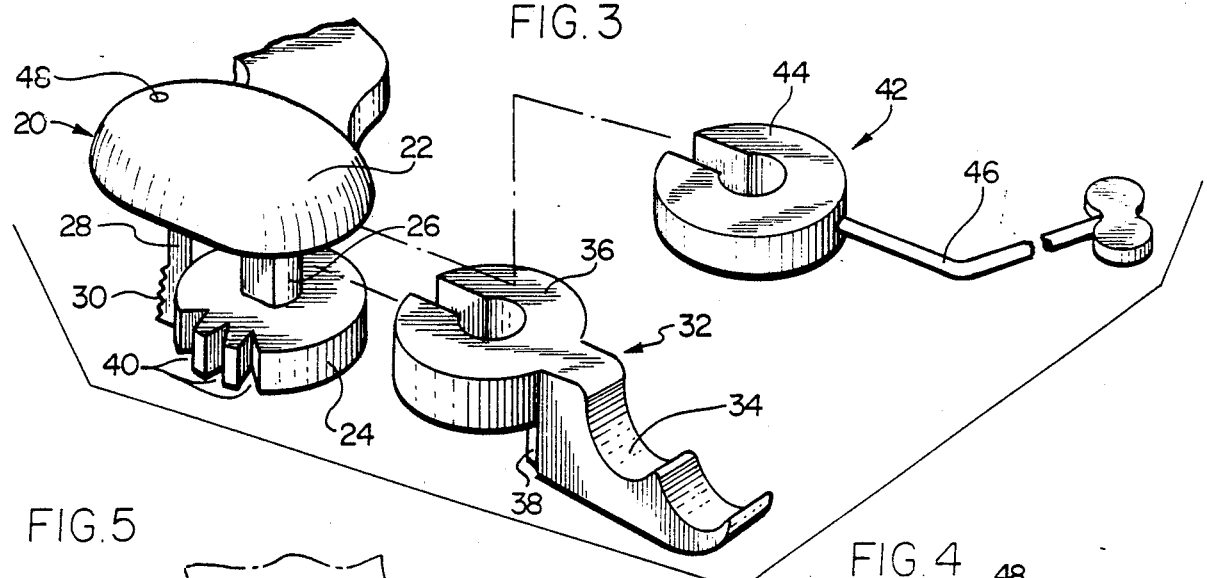
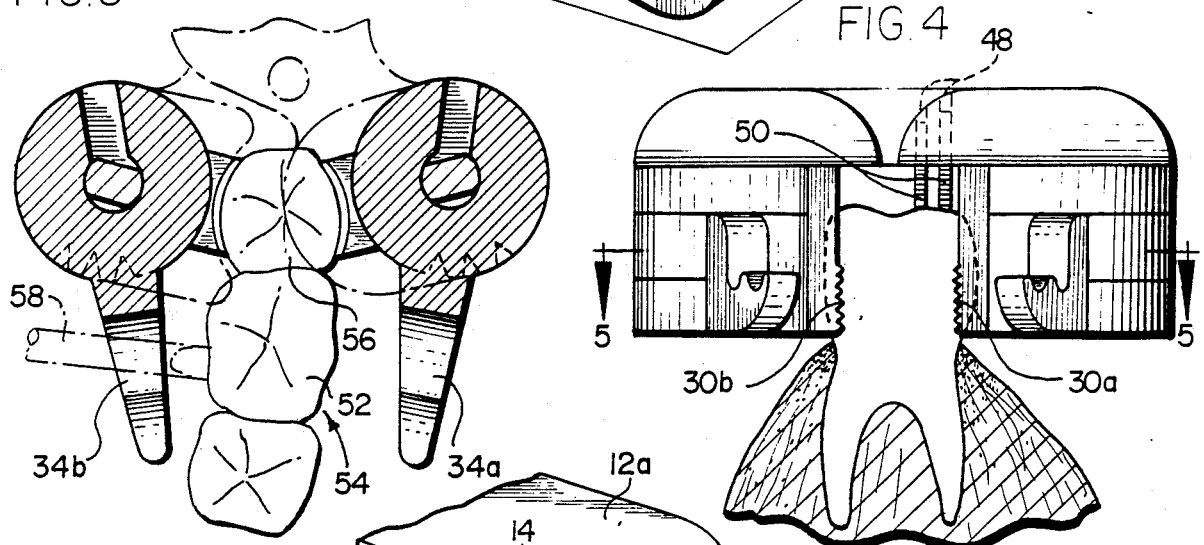
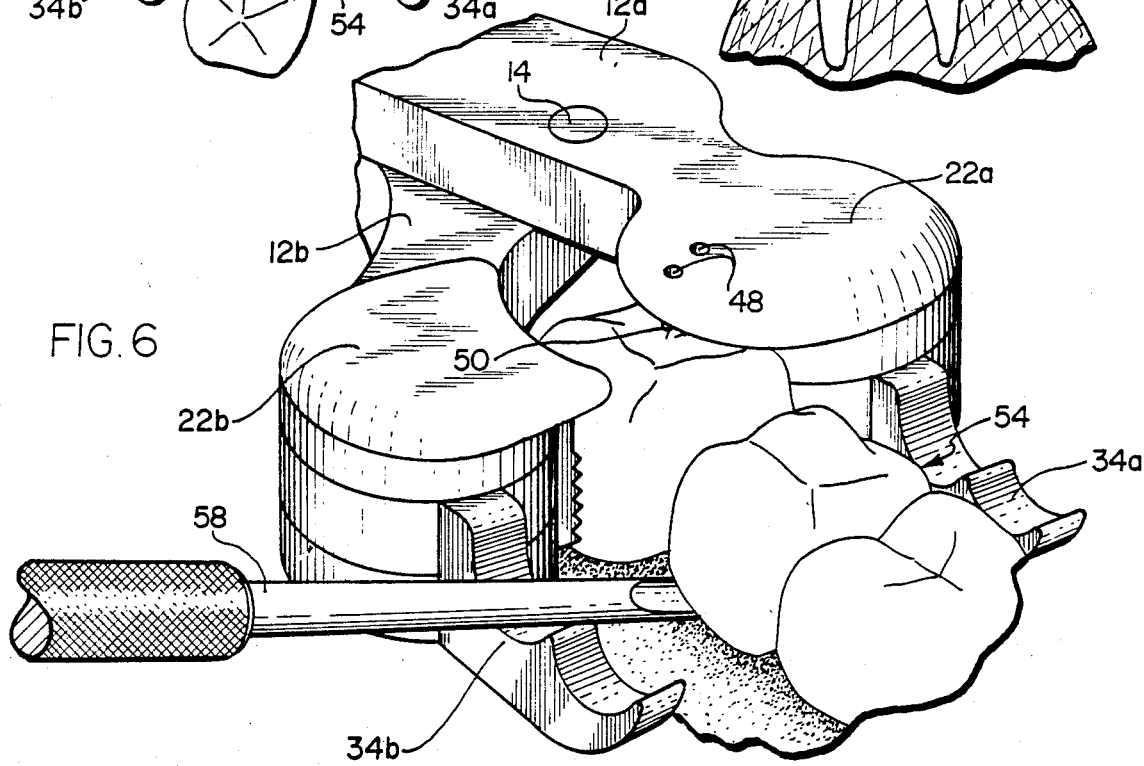

DENTAL INSTRUMENT

BACKGROUND OF THE INVENTION

The present invention relates generally to improved methods and devices for the removal of dental crowns from teeth. Traditional methods for the removal of dental crowns include those such as the following.

Anderson, U.S. Pat. No. 4,179,816 discloses a method for the removal of crowns wherein a hole is made in the occlusal surface of the crown and the margins of that crown are undercut in order that a device with lateral projections may be inserted to lift the remaining portion of the crown off the tooth.

Lococo, U.S. Pat. No. 4,230,454 discloses a method for removal of teeth whereby indentations are drilled in the buccal and lingual sides of a tooth. A tool with the two hemispherical tips for engaging the indentations so drilled is attached to the tooth which is then extracted by application of force on the instrument utilizing a plate placed across adjacent teeth as a fulcrum.

Brantley, U.S. Pat. No. 2,430,271 discloses a device for extraction of teeth comprising pivoting, opposing clamping members for attachment to a tooth to be removed. A lever supported by a base on an adjacent tooth is used to lift the clamping members, vertically removing the tooth.

Lynch, U.S. Pat. No. 4,474,500 discloses a method by which a porcelain crown is removed by means of a noose which is lifted upwardly from the tooth while pressing down against a screw drilled through the crown and resting on the tooth stub below.

Planert, PCT Abstract of WO 87/02573 discloses a device for removing crowns comprising an extraction frame to which two mutually opposed folding jaws are provided to ensure a grip on the crown. The device further comprises a movably supported mass which is guided in a movement track to strike an anvil linked to the extraction frame. The impact of the movable mass against the anvil serves to break the cement bond of the crown with the tooth stub.

Machat, U.S. Pat. No. 2,172,478 discloses a long-handled tooth extracting instrument comprising a metal end which is inserted into a hole drilled in the tooth to be removed. The instrument further comprises a spur and a protective covering which are rested on the top of the tooth adjacent from that to be removed. The adjacent tooth is then used as a fulcrum and the instrument is utilized to apply a large amount of force and thus remove the tooth.

Goldenthal, U.S. Pat. No. 4,197,647 discloses curved, scissors-like dental pliers having a pair of fulcral projections to the rear of the pivot point. The pliers include cushioning pads for gripping dental work such as crowns. The dental work may be removed by gripping with the cushioning pads and using the pliers as a lever forcing the fulcral projections down onto a support member placed across teeth across the mouth from that subjected to the procedure.

Such traditional methods for the removal of crowns tend to be less than completely satisfactory for a number of reasons. Such methods may tend to damage or destroy crowns or may be overly complex in their execution. For those reasons, there exists a need for an improved method for the removal of dental crowns.

SUMMARY OF THE INVENTION

The present invention provides a dental instrument to be utilized in conjunction with other dental instruments such as those known as "elevators" for the removal of crowns and other dental prostheses. The instrument of the invention is adjustable and is attached to a tooth adjacent to the tooth having the crown to be removed. The scissors-like device of the invention includes a pair of opposed gripping projections for firm attachment to a tooth and may have a set of locking arms so that one need not constantly maintain manual pressure to secure attachment. The instrument presents a pair of tools having adjustable tongue-like projections which are to be projected adjacent to the tooth from which the crown is to be removed. The tongues provide a strong, stable surface that can be used as a fulcrum by one elevator applied to each side of the crown serially, or two elevators applied to both sides of the crown simultaneously. Pressure is applied by the elevator(s) at the margin of the crown and the tooth stub such that the cement bond between the two is broken. The present instrument thus provides an improved method for the non-destructive removal of crowns and other dental prostheses.

BRIEF DESCRIPTION OF THE DRAWING

FIG. 1 is a plan view of the dental instrument of the invention.

FIG. 2 is a view taken along line 2—2 of FIG. 1.

FIG. 3 is an exploded view of the instrument mounting head of the dental instrument.

FIG. 4 is a view of the dental instrument clamped onto a tooth.

FIG. 5 is a view along line 5—5 of FIG. 4 of the dental instrument clamped onto a tooth and the instrument supporting an elevator which is contacted with an adjacent tooth.

FIG. 6 is a perspective view of the dental instrument clamped onto a first tooth and the instrument supporting an elevator which is being used to remove a crown from an adjacent tooth.

DETAILED DESCRIPTION

Referring to FIG. 1, a dental instrument (10) according to the present invention comprises a pair of arms (12ab) pivotably joined at a pivot (14) to define a scissors-like implement, the arms rotating about axis 14a in pivot 14. It should be noted that the arms lie essentially in a single plane, defining said plane. Each of the arms 12a and 12b has a handle portion (16ab) terminating in finger rings (18ab) which may also optionally be fitted with sliding locking elements (19ab) such that the instrument may be locked in tension about a tooth.

Referring to FIGS. 2 and 3, the arms each include an instrument mounting head (20) comprising an upper head member (22) and a lower head member (24) connected by a tool mounting post (26) located centrally between the upper and lower head members and a clamping post (28) located at the edge of the upper and lower head members. The clamping post may comprise gripping projections (30) for attachment to a tooth. Alternatively, such gripping projections may optionally be an aspect of an insert, such as may be fabricated from a metal such as tungsten carbide and may be inserted at the clamping post.

Attached to the tool mounting post (26) is a tool (32) comprising a tongue (34) and a slotted circular joining member (36). At the base of the slotted circular joining member is a locking projection (38). The tool (32) may be mounted on the head by mating of the tool mounting post (26) with the slotted circular joining member (36). The radial orientation of the tool is fixed by mating of the locking projection (38) with one of several locking slots (40). The tool is located in place, and axial motion of the tool is fixed by mating of the slotted circular locking band (42) with the tool mounting post (26). The locking band (42) comprises a slotted circular member (44) and an elongated handle (46).

In preparation of the device for use, the tool (32) is inserted over the tool mounting post (26), is rotated to align the locking projection (38) with a selected locking slot (40), thus locking the tool (32) onto the tool mounting post, and is slid axially down the tool mounting post to engage projection (38) with a selected locking slot (40) so as to prevent rotation of the tool (32) around the mounting post (26). The locking band (42) is then inserted around the tool mounting post (26) and rotated so as to lock itself onto the tool mounting post, preferably with the elongated handle (46) secured under the arm (12). Insertion and locking of the locking band (42) onto the tool mounting post (26) puts axial pressure onto the slotted member (36) of the tool ensuring that it is fixed into place. At the upper head member (22a) of one of the arms (12a) are threaded holes (48) through which screws (50) may be inserted for gauging the distance that the instrument can extend on an adjacent tooth by extending or shortening the length of the screws.

According to a method for use of the instrument (10) to assist in removal of a dental crown (52) from a first tooth (54) (see FIGS. 5 and 6), the tools (32ab) are fixed in their respective heads (20ab) and locked by means of the locking bands (42ab). The instrument is then used to grip a second tooth (56) adjacent to the first tooth (54) by means of compression of the two sets of gripping projections (30ab) against either side of the second tooth (56). The instrument is used to grip the second tooth (56) in a fashion such that the tongues (34ab) of the tool are aligned generally even with the edge of the dental crown. A dental instrument such as what is known in the art as an elevator (58) is then rested on the tongue (34) of the instrument which provides a steady, solid base for the elevator and the elevator is inserted at the margin between the crown (52) and the first tooth (54). With the tongue (34) providing a fulcrum, the elevator (58) is used to apply pressure to break the cement bond between the crown and the tooth and to pry the crown (52) off of the tooth. Using a single elevator, pressure may be applied first to one side of the crown using one tongue of the instrument (10) and then to the other. Alternatively, two elevators may be used to apply pressure to the crown from both the lingual and facial surfaces simultaneously.

Force may be applied to the elevator (58) to break the bond of the crown and the tooth with force transmitted to all the lingual and facial surfaces of the margins of the crown. Ultrasonic vibrations may also be used to transmit bond breaking energy to the margin of the crown.

The instrument has multiple and adjustable positions that suit it for use with a variety of teeth and crowns. While the device is illustrated such that both tools (32) are adjustable and comprise multiple radial locking slots, one or both of the tools may optionally be fixed to the mounting head (20). The screws 50 may be set to limit the gingival direction of the tongues (34). The instrument may also be preset by making a mold and model of the dentition.

The preferred material for the construction of the instrument is surgical stainless steel which allows sterilization of the instrument in an autoclave. The gripping projections are preferably fabricated from tungsten carbide.

It will be seen by one of skill in the art that numerous modifications may be made in the construction and use of the instrument without departing from the spirit and scope of the invention. Consequently, only such limitations as appear in the appended claims should be placed on the invention.

What is claimed is:

1. A dental instrument for attachment to a first tooth and providing a stable support for the use of other dental instruments comprising:

a pair of arms, each arm having a handle portion and an adjustable instrument mounting head portion comprising opposable tooth gripping means for gripping said first tooth, an upper head member, a lower head member, a tool mounting post located axially and attached between the upper and lower head members, a clamping post attached between the upper and lower head members and located laterally from the tool mounting post wherein said gripping means are attached to said clamping post, and a tool comprising a tongue extending beyond said gripping means to a position adjacent to a second tooth for providing a stable fulcrum for a dental instrument used to pry a dental prosthesis from said second tooth; and pivot means joining said arms for rotation relative to each other.

2. The dental instrument according to claim 1 wherein each of said tools comprises a slotted joining member suitable for attachment to said tool mounting post.

3. The dental instrument according to claim 2 wherein at least one of said lower head members comprises locking slots and wherein said corresponding tool comprises a locking projection suitable for mating with said locking slot when the slotted joining member of said tool is engaged with the tool mounting post.

4. The dental instrument according to claim 3 further comprising a locking band which may be engaged with said tool mounting post to secure the slotted joining member of the tool against motion.

5. The dental instrument according to claim 1 wherein at least one of said upper head members of the instrument mounting heads comprises screws for adjusting the vertical position of the instrument.

6. A dental instrument for attachment to a first tooth and providing a stable support for the use of other dental instruments comprising:

a pair of arms, each arm having a handle portion and an adjustable instrument mounting head portion comprising:

an upper head member, a lower head member, a tool mounting post located axially and attached between the upper and lower head members, a clamping post attached between the upper and lower head members and located laterally from the tool mounting post wherein tooth gripping means are attached to said clamping post;

a tool comprising a tongue extending beyond said gripping means to a position adjacent to a second tooth for providing a stable fulcrum for a dental instrument used to pry a dental prosthesis from said second tooth and a slotted joining member suitable for attachment to said tool mounting post wherein said lower head member comprises a locking projection suitable for mating with said locking slot when the slotted joining member of said tool is engaged with the tool mounting post, said instrument further comprising a locking band which may be engaged with said tool mounting post to secure the slotted joining member of the tool against motion; and pivot means joining said arms for rotation relative to each other.

7. A method of removing dental prostheses from teeth to which they are bonded comprising the steps of
   (a) attaching a dental instrument according to claim 1 to a first tooth such that the tongues of the tool elements providing stable support for dental instruments are adjacent to a second tooth from which the prosthesis is to be removed, and
   (b) applying pressure to the margin between the second tooth and prosthesis with a prying instrument utilizing a tongue of the tool as a fulcrum.

8. The method of claim 7 wherein said dental prosthesis is a crown.

* * * * *

UNITED STATES PATENT AND TRADEMARK OFFICE
CERTIFICATE OF CORRECTION

PATENT NO. : 4,923,399

DATED : May 8, 1990

INVENTOR(S) : Funderburg, Jr.

It is certified that error appears in the above-identified patent and that said Letters Patent is hereby corrected as shown below:

Column 5, line 4, after "comprises" insert --locking slots and wherein said tool comprises--.

Signed and Sealed this

Eighth Day of October, 1991

Attest:

HARRY F. MANBECK, JR.

*Attesting Officer*  *Commissioner of Patents and Trademarks*